United States Patent
Minagawa et al.

(10) Patent No.: US 11,643,660 B2
(45) Date of Patent: May 9, 2023

(54) NUCLEOSIDE DERIVATIVE OR SALT THEREOF, POLYNUCLEOTIDE SYNTHESIS REAGENT, METHOD FOR PRODUCING POLYNUCLEOTIDE, POLYNUCLEOTIDE, AND METHOD FOR PRODUCING BINDING NUCLEIC ACID MOLECULE

(71) Applicants: NEC Solution Innovators, Ltd., Tokyo (JP); National University Corporation Gunma University, Gunma (JP)

(72) Inventors: Hirotaka Minagawa, Tokyo (JP); Katsunori Horii, Tokyo (JP); Jou Akitomi, Tokyo (JP); Naoto Kaneko, Tokyo (JP); Iwao Waga, Tokyo (JP); Masayasu Kuwahara, Gunma (JP)

(73) Assignees: NEC SOLUTION INNOVATORS, LTD., Tokyo (JP); NATIONAL UNIVERSITY CORPORATION GUNMA UNIVERSITY, Gunma (JP)

( * ) Notice: Subject to any disclaimer, the term of this patent is extended or adjusted under 35 U.S.C. 154(b) by 943 days.

(21) Appl. No.: 16/464,057

(22) PCT Filed: Oct. 12, 2017

(86) PCT No.: PCT/JP2017/037093
§ 371 (c)(1),
(2) Date: May 24, 2019

(87) PCT Pub. No.: WO2018/096831
PCT Pub. Date: May 31, 2018

(65) Prior Publication Data
US 2019/0382765 A1    Dec. 19, 2019

(30) Foreign Application Priority Data

Nov. 28, 2016   (JP) .............................. JP2016-230196

(51) Int. Cl.
| | | |
|---|---|---|
| C07H 19/10 | (2006.01) | |
| C07H 19/20 | (2006.01) | |
| C12N 15/115 | (2010.01) | |
| C12N 15/10 | (2006.01) | |
| C07H 1/00 | (2006.01) | |
| C07H 21/00 | (2006.01) | |
| C07H 21/04 | (2006.01) | |
| C07H 21/02 | (2006.01) | |

(52) U.S. Cl.
CPC ............. *C12N 15/115* (2013.01); *C07H 1/00* (2013.01); *C07H 19/20* (2013.01); *C07H 21/00* (2013.01); *C07H 21/02* (2013.01); *C07H 21/04* (2013.01); *C12N 15/1048* (2013.01)

(58) Field of Classification Search
None
See application file for complete search history.

(56) References Cited

U.S. PATENT DOCUMENTS

2005/0130195 A1   6/2005   Fujihara et al.
2016/0311845 A1   10/2016  Kuwahara

FOREIGN PATENT DOCUMENTS

| JP | 2012-200204 A | | 10/2012 |
|---|---|---|---|
| JP | 2013-40118 | * | 2/2013 |
| JP | 2013-040118 A | | 2/2013 |
| JP | 2016-056136 A | | 4/2016 |
| JP | 201656136 | * | 4/2016 |

(Continued)

OTHER PUBLICATIONS

Uwahara, Masayasu, "Polymer Reprogramming: Developmentof Nucleic Acid Aptamers Incorporating Non-Natural Molecules", Polymers, 2014, vol. 63, No. 10, pp. 7 3 0, 7 31.*

(Continued)

*Primary Examiner* — Traviss C McIntosh, III
(74) *Attorney, Agent, or Firm* — Wilmer Cutler Pickering Hale and Dorr LLP

(57) ABSTRACT

The present invention provides a novel nucleoside derivative or a salt thereof, a polynucleotide synthesis reagent, a method for producing a polynucleotide, a polynucleotide, and a method for producing a binding nucleic acid molecule. The nucleoside derivative or a salt thereof of the present invention is represented by the following chemical formula (1).

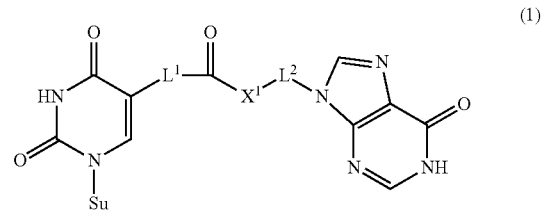

(1)

In the chemical formula (1), Su is an atomic group having a sugar skeleton at a nucleoside residue or an atomic group having a sugar phosphate skeleton at a nucleotide residue, and may or may not have a protecting group, $L^1$ and $L^2$ are each independently a straight-chain or branched, saturated or unsaturated hydrocarbon group having 2 to 10 carbon atoms, $X^1$ is an imino group (—$NR^1$—), an ether group (—O—), or a thioether group (—S—), and $R^1$ is a hydrogen atom or a straight-chain or branched, saturated or unsaturated hydrocarbon group having 2 to 10 carbon atoms.

14 Claims, 5 Drawing Sheets
Specification includes a Sequence Listing.

(56) References Cited

FOREIGN PATENT DOCUMENTS

| WO | WO-2015/064223 A1 | | 5/2015 | |
| WO | WO-2015064223 A1 | * | 5/2015 | ........... C07H 19/073 |
| WO | WO-2018/051569 A1 | | 3/2018 | |

OTHER PUBLICATIONS

Imaizumi et al., JACS, 2013 vol. 135(25) pp. 9412-9419. (Year: 2013).*
Extended European Search Report issued in European Patent Application No. 17850964.2 dated May 14, 2019, 9 pages.
Extended European Search Report issued in European Patent Application No. 17850965.9 dated May 13, 2019, 8 pages.
International Search Report corresponding to PCT/JP2017/037093 dated Nov. 21, 2017 (2 pages).
Imaizumi, Y. et al., "Efficacy of Base-Modification on Target Binding of Small Molecule DNA Aptamers", Journal of the American Chemical Society, vol. 135, No. 25, (2013) (pp. 9412-9419).
Kuwahara, Masayasu "Creation of Nucleic Acid Aptamers That Contain Unnatural Nucleotides", Polymers, vol. 63, No. 10, (Oct. 2014) (5 pages).
Extended European Search Report issued in European Patent Application No. 17874515.4, dated Sep. 26, 2019, 8 pages.

* cited by examiner

SEQUENCE LISTING

<160> NUMBER OF SEQ ID NOS: 4

<210> SEQ ID NO 1
<211> LENGTH: 77
<212> TYPE: DNA
<213> ORGANISM: Artificial Sequence
<220> FEATURE:
<223> OTHER INFORMATION: Synthesized polynucleotide

<400> SEQUENCE: 1
ggaatcagtc cgccgctaat acgctggtat ggttgaagtg cgtattagac atgtgaacga      60
tcctgtgccc gataaag                                                    77

<210> SEQ ID NO 2
<211> LENGTH: 77
<212> TYPE: DNA
<213> ORGANISM: Artificial Sequence
<220> FEATURE:
<223> OTHER INFORMATION: Synthesized polynucleotide

<400> SEQUENCE: 2
ggaatcagtc cgccgctaat actagtcatc gcttttaatt tcgcattgta ccgtgaacga      60
tcctgtgccc gataaag                                                    77

<210> SEQ ID NO 3
<211> LENGTH: 72
<212> TYPE: DNA
<213> ORGANISM: Artificial Sequence
<220> FEATURE:
<223> OTHER INFORMATION: Synthesized polynucleotide

<400> SEQUENCE: 3
ggtaagactc ccgccagatt tgggtggggg gcggggtgg aggaggtggc ggtgaagccc       60
tcggtcgaaa tc                                                         72

<210> SEQ ID NO 4
<211> LENGTH: 75
<212> TYPE: DNA
<213> ORGANISM: Artificial Sequence
<220> FEATURE:
<223> OTHER INFORMATION: Synthesized polynucleotide

```
<400> SEQUENCE: 4
ggaaaccctg cgtcctgaaa ttgcgctgcg atagtgaagg cataacaggt tcactcatct    60
gtgctggcgg aatag                                                    75
```

NUCLEOSIDE DERIVATIVE OR SALT THEREOF, POLYNUCLEOTIDE SYNTHESIS REAGENT, METHOD FOR PRODUCING POLYNUCLEOTIDE, POLYNUCLEOTIDE, AND METHOD FOR PRODUCING BINDING NUCLEIC ACID MOLECULE

CROSS REFERENCE-TO RELATED APPLICATIONS

This application is a national stage application of International Application No. PCT/JP2017/037093 entitled "Nucleoside Derivative or Salt Thereof, Polynucleotide Synthesis Reagent, Method for Producing Polynucleotide, Polynucleotide, and Method for Producing Binding Nucleic Acid Molecule" filed on Oct. 12, 2017, which claims priority to Japanese Patent Application No. 2016-230196 filed on Nov. 28, 2016, the disclosures of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 22, 2019 is named TF16098US_Sequence Listing.txt and is 1563 bytes in size.

TECHNICAL FIELD

The present invention relates to a nucleoside derivative or a salt thereof, a polynucleotide synthesis reagent, a method for producing a polynucleotide, a polynucleotide, and a method for producing a binding nucleic acid molecule.

BACKGROUND ART

In order to analyze a target in a specimen, a binding molecule that binds to a target is used. In addition to an antibody, a binding nucleic acid molecule that binds to a target such as an aptamer is also used as a binding molecule that binds to the target (Patent Literature 1).

As a method for obtaining the binding nucleic acid molecule, a SELEX (Systematic Evolution of Ligands by Exponential Enrichment method) in which a target is caused to come into contact with a large number of candidate polynucleotides and a polynucleotide that binds to the target among the candidate polynucleotides is selected as the binding nucleic acid molecule is known. When a binding nucleic acid molecule is obtained by the SELEX method, a modified nucleoside molecule obtained by modifying a natural nucleoside molecule is also used in addition to a natural nucleoside molecule that constitutes the binding nucleic acid molecule.

However, with known natural nucleosides and derivatives thereof, there are targets for which binding nucleic acid molecules with sufficient binding ability cannot be obtained. Therefore, there is a need for modified nucleoside derivatives that can be used, for example, in the production of aptamers.

CITATION LIST

Patent Literature

Patent Literature 1: JP 2012-200204 A

SUMMARY OF INVENTION

Technical Problem

Hence, the present invention is intended to provide a novel nucleoside derivative or a salt thereof, a polynucleotide synthesis reagent, a method for producing a polynucleotide, a polynucleotide, and a method for producing a binding nucleic acid molecule.

Solution to Problem

The nucleoside derivative or a salt thereof of the present invention is represented by the following chemical formula (1).

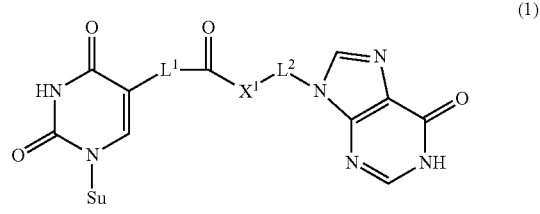

(1)

In the chemical formula (1), Su is an atomic group having a sugar skeleton at a nucleoside residue or an atomic group having a sugar phosphate skeleton at a nucleotide residue, and may or may not have a protecting group, $L^1$ and $L^2$ are each independently a straight-chain or branched, saturated or unsaturated hydrocarbon group having 2 to 10 carbon atoms, $X^1$ is an imino group (—$NR^1$—), an ether group (—O—), or a thioether group (—S—), and $R^1$ is a hydrogen atom or a straight-chain or branched, saturated or unsaturated hydrocarbon group having 2 to 10 carbon atoms.

The polynucleotide synthesis reagent of the present invention includes a nucleotide derivative or a salt thereof including the nucleoside derivative or a salt thereof of the present invention.

The method for producing a polynucleotide of the present invention includes the step of synthesizing a polynucleotide using a nucleotide derivative or a salt thereof including the nucleoside derivative or a salt thereof of the present invention.

The polynucleotide of the present invention includes, as a building block, a nucleotide derivative or a salt thereof including the nucleoside derivative or a salt thereof of the present invention.

A method for producing a binding nucleic acid molecule of the present invention includes the steps of causing a candidate polynucleotide and a target to come into contact with each other, and selecting a candidate polynucleotide bound to the target as a binding nucleic acid molecule that binds to the target, and the candidate polynucleotide is the polynucleotide of the present invention.

Advantageous Effects of Invention

The present invention can provide a novel nucleoside derivative or a salt thereof.

Figure 1A:
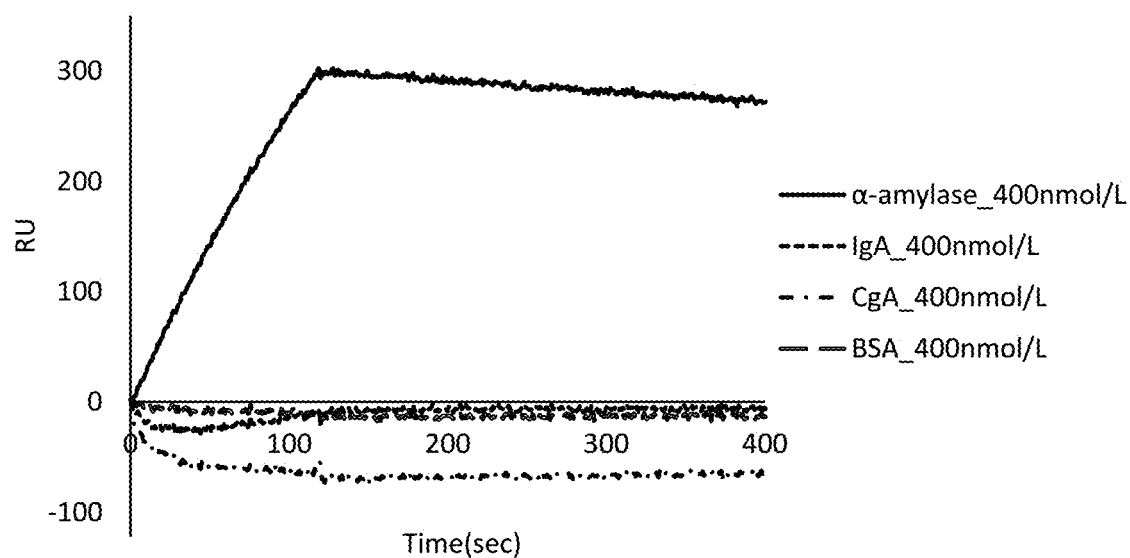
FIGS. 1A and 1B are graphs illustrating the binding ability of the α-amylase-binding nucleic acid molecule to amylase in Example 2.

DESCRIPTION OF EMBODIMENTS (Nucleoside Derivative or Salt Thereof)

The nucleoside derivative or a salt thereof of the present invention is represented by the following chemical formula (1), as mentioned above.

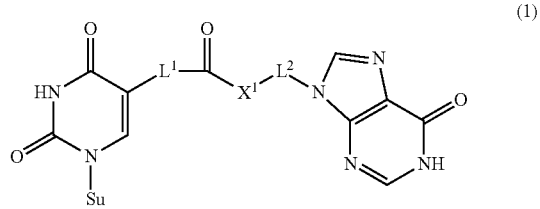

(1)

In the chemical formula (1), Su is an atomic group having a sugar skeleton at a nucleoside residue or an atomic group having a sugar phosphate skeleton at a nucleotide residue, and may or may not have a protecting group, $L^1$ and $L^2$ are each independently a straight-chain or branched, saturated or unsaturated hydrocarbon group having 2 to 10 carbon atoms, $X^1$ is an imino group (—$NR^1$—), an ether group (—O—), or a thioether group (—S—), and $R^1$ is a hydrogen atom or a straight-chain or branched, saturated or unsaturated hydrocarbon group having 2 to 10 carbon atoms.

The nucleoside derivative of the present invention has two of a purine ring-like structure and a pyrimidine ring-like structure. The nucleoside derivative of the present invention thus has, for example, a relatively larger number of atoms capable of interacting within or between molecules than a nucleoside derivative having one purine ring-like structure or one pyrimidine ring-like structure. The binding nucleic acid molecule including the nucleoside derivative of the present invention therefore has an improved binding ability to a target, for example, compared to a nucleoside derivative having one purine ring-like structure or one pyrimidine ring-like structure. Thus, with the nucleoside derivative of the present invention, a binding nucleic acid molecule that exhibits excellent binding ability to a target can be produced, for example.

In the chemical formula (1), $L^1$ and $L^2$ are each independently a straight-chain or branched, saturated or unsaturated hydrocarbon group having 2 to 10 carbon atoms. The lower limit of the number of carbon atoms of $L^1$ is 2, the upper limit of the same is 10, preferably 8 or 6, and the range of the same is, for example, 2 to 8, 2 to 6. The number of carbon atoms of $L^1$ is preferably 2. The lower limit of the number of carbon atoms of $L^2$ is 2, the upper limit of the same is 10, preferably 8 or 6, and the range of the same is, for example, 2 to 8, 2 to 6. The number of carbon atoms of $L^2$ is preferably 2. Specific examples of $L^1$ and $L^2$ include an ethylene group (—$CH_2$—$CH_2$—), a vinylene group (—CH=CH—), a propylene group (—$CH_2$—$CH_2$—$CH_2$—), an isopropylene group (—$CH_2$—CH($CH_3$)—), a butylene group (—$CH_2$—$CH_2$—$CH_2$—$CH_2$—), a methylbutylene group (—$CH_2$—CH($CH_3$)—$CH_2$—$CH_2$—), a dimethylbutylene group (—$CH_2$—CH($CH_3$)—CH($CH_3$)—$CH_2$—), an ethylbutylene group (—$CH_2$—CH($C_2H_5$)—$CH_2$—$CH_2$—), a pentylene group (—$CH_2$—$CH_2$—$CH_2$—$CH_2$—$CH_2$—), a hexylene group (—$CH_2$—$CH_2$—$CH_2$—$CH_2$—$CH_2$—$CH_2$—), a heptylene group (—$CH_2$—$CH_2$—$CH_2$—$CH_2$—$CH_2$—$CH_2$—$CH_2$—), and an octylene group (—$CH_2$—$CH_2$—$CH_2$—$CH_2$—$CH_2$—$CH_2$—$CH_2$—$CH_2$—). $L^1$ is preferably a vinylene group (—CH=CH—). $L^2$ is preferably an ethylene group (—$CH_2$—$CH_2$—). $L^1$ and $L^2$ may be the same hydrocarbon group or different hydrocarbon groups. As a specific example of the latter, $L^1$ is preferably a vinylene group (—CH=CH—), and $L^2$ is preferably an ethylene group (—$CH_2$—$CH_2$—).

In the chemical formula (1), $X^1$ is an imino group (—$NR^1$—), an ether group (—O—), or a thioether group (—S—). In the imino group, the R1 is a hydrogen atom or a straight-chain or branched, saturated or unsaturated hydrocarbon group having 2 to 10 carbon atoms and is preferably a hydrogen atom. The description of $L^1$ and $L^2$ can be incorporated in the description of the straight-chain or branched, saturated or unsaturated hydrocarbon group having 2 to 10 carbon atoms by reference. $X^1$ is preferably an imino group (—$NR^1$—). $X^1$ is more preferably an NH group.

In the chemical formula (1), the atomic group having a sugar skeleton at a nucleoside residue is not particularly limited, and examples thereof include atomic groups having sugar skeletons on known natural or artificial nucleoside residues. Examples of the atomic group having a sugar skeleton at a natural nucleoside residue include an atomic group having a ribose skeleton at a ribonucleoside residue and an atomic group having a deoxyribose skeleton on a deoxyribonucleoside. The atomic group having a sugar skeleton at an artificial nucleoside residue can be, for example, an atomic group having a bicyclic sugar skeleton at an artificial nucleoside residue, and specific examples thereof can be an atomic group having a ribose skeleton where an oxygen atom at 2'-position and a carbon atom at 4' position of ENA (2'-O,4'-C-Ethylene-bridged Nucleic Acids) or LNA (Locked Nucleic Acid) is crosslinked. The atomic group having a sugar phosphate skeleton at a nucleotide residue is not particularly limited, and examples thereof include atomic groups having sugar phosphate skeletons at known natural or artificial nucleotide residues. Examples of the atomic group having a sugar phosphate skeleton at a natural nucleotide residue include an atomic group having a ribose phosphate skeleton at a ribonucleotide residue and an atomic group having a deoxyribose phosphate skeleton on a deoxyribonucleotide. The atomic group having a sugar phosphate skeleton at an artificial nucleotide residue can be, for example, an atomic group having a bicyclic sugar phosphate skeleton at an artificial nucleoside residue, and specific examples thereof can be an atomic group having a ribose phosphate skeleton where an oxygen atom at 2'-position and a carbon atom at 4' position of 2'-O,4'-C-Ethylene-bridged Nucleic Acids (ENA) or Locked Nucleic Acid (LNA) is crosslinked.

In the chemical formula (1), an atomic group having a sugar skeleton at a nucleoside residue or an atomic group having a sugar phosphate skeleton at a nucleotide residue is represented by preferably the following chemical formula (2).

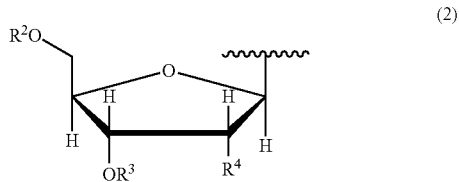

(2)

In the chemical formula (2), $R^2$ is a hydrogen atom, a protecting group, or a group represented by the following chemical formula (3), $R^3$ is a hydrogen atom, a protecting group, or a phosphoramidite group, $R^4$ is a hydrogen atom, a fluorine atom, a hydroxyl group, an amino group, or a mercapto group.

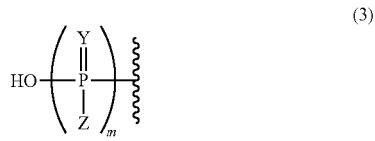

(3)

In the chemical formula (3), Y is an oxygen atom or a sulfur atom, Z is a hydroxyl group or an imidazole group, and m is an integer of 1 to 10.

In the chemical formula (2), $R^2$ is a hydrogen atom, a protecting group, or a group represented by the following chemical formula (3). The protecting group is not particularly limited and can be, for example, a protecting group of a known hydroxyl group used in nucleic acid synthesis methods, and as a specific example, the protecting group can be a DMTr group (4,4'-dimethoxy(triphenylmethyl) group). When $R^2$ is a group represented by the chemical formula (3), the nucleoside derivative of the present invention can also be referred to as a nucleotide derivative, for example.

In the chemical formula (2), $R^3$ is a hydrogen atom, a protecting group, or a phosphoramidite group. The protecting group is not particularly limited, and, the description of $R^2$ can be incorporated in the description of the protecting group by reference, for example. The phosphoramidite group is represented by the chemical formula (5). When $R^3$ is a phosphoramidite group, the nucleoside derivative of the present invention can also be referred to as a phosphoramidite compound of the nucleoside derivative, for example. When $R^2$ is a group represented by the chemical formula (3), and $R^3$ is a phosphoramidite group, the nucleoside derivative of the present invention can also be referred to as, for example, a phosphoramidite compound of the nucleotide derivative.

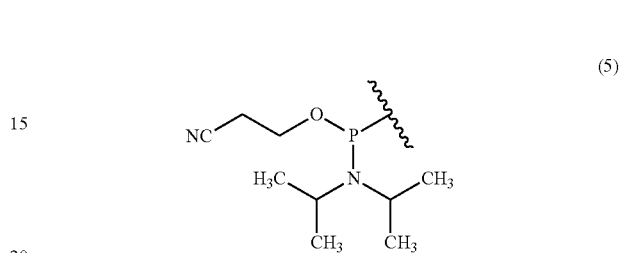

(5)

In the chemical formula (2), $R^4$ is a hydrogen atom, a fluorine atom, a hydroxyl group, an amino group, or a mercapto group and is preferably a hydrogen atom or a hydroxyl group. When $R^4$ is a hydrogen atom, the nucleoside derivative of the present invention has a deoxyribose skeleton as a sugar skeleton and can be used for, for example, synthesis of DNAs. When $R^4$ is a hydroxyl group, the nucleoside derivative of the present invention has a ribose skeleton as a sugar skeleton and can be used for, for example, synthesis of RNAs.

In the chemical formula (3), Y is an oxygen atom or a sulfur atom. When Y is an oxygen atom, polynucleotide including, as a building block, the nucleoside derivative of the present invention can also be referred to as polynucleotide having a phosphodiester bond. When Y is a sulfur atom, polynucleotide including, as a building block, the nucleoside derivative of the present invention can also be referred to as polynucleotide having a phosphorothioate bond.

In the chemical formula (3), Z is a hydroxyl group or an imidazole group. In the imidazole group, imidazole is bound to a phosphate atom via a nitrogen atom at the 1-position, for example.

In the chemical formula (3), m is an integer of 1 to 10, preferably 1 to 3, 1 to 2, or 1.

The nucleoside derivative of the present invention is represented by preferably the following chemical formula (4). The nucleoside derivative represented by the following formula (4) is also referred to as IA8.

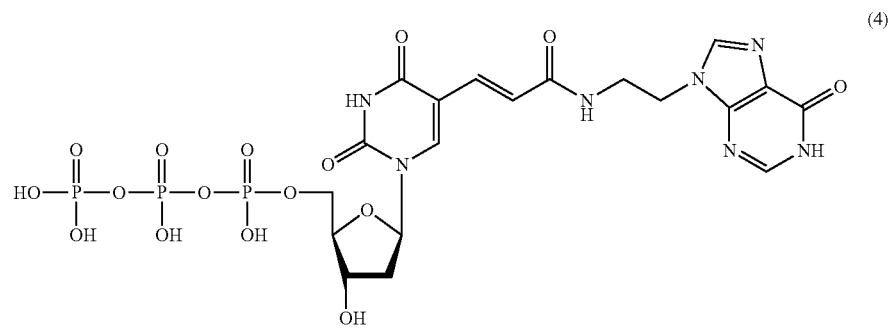 [SMILES: O=C(/C=C/c1cn([C@H]2C[C@@H](O)[C@@H](COP(=O)(O)OP(=O)(O)OP(=O)(O)O)O2)c(=O)[nH]c1=O)NCCn1cnc2c(=O)[nH]cnc21]

(4)

The nucleoside derivative or a salt thereof of the present invention may be a stereoisomer such as enantiomers, tautomers, geometric isomers, conformers, and optical isomers thereof, and salts thereof. Specifically, in the chemical formula (1) and chemical formulae described below, the sugar skeleton is D body, but the nucleoside derivative of the present invention is not limited thereto, and the sugar skeleton may be L body.

The salt of the nucleoside derivative of the present invention may be an acid addition salt or a base addition salt. Further, acid which forms the acid addition salt may be an inorganic acid or an organic acid, and base which forms the base addition salt may be an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodine acid, perfluoric acid, perchloric acid, perbromic acid, and periodic acid. The organic acid is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxides, alkali metal hydroxides, alkaline earth metal hydroxides, carbonates, and bicarbonates. More specific examples thereof include sodium hydroxide, potassium hydroxide, potassium carbonate, sodium carbonate, sodium bicarbonate, potassium hydrogen carbonate, calcium hydroxide, and calcium carbonate. The organic base is not particularly limited, and examples thereof include ethanolamine, triethylamine, and tris(hydroxymethyl)aminomethane.

The method for producing the nucleoside derivative of the present invention is not particularly limited, and the nucleoside derivative of the present invention can be produced by combining known synthesis methods. As a specific example, the nucleoside derivative of the present invention can be synthesized by, for example, producing a thymidine derivative through a reaction including 4 stages using 6-chloropurine as a starting material and then triphosphorylating a hydroxyl group at 5' position of the thymidine derivative and removing a protecting group at the O6 position of the thymidine derivative such as a synthesis method of the examples to be described below.

(Polynucleotide Synthesis Reagent)

The polynucleotide synthesis reagent (hereinafter also referred to as "synthesis reagent") of the present invention contains a nucleotide derivative or a salt thereof including the nucleoside derivative or a salt thereof of the present invention, as mentioned above. The synthesis reagent of the present invention is characterized by containing the nucleoside derivative of the present invention, and other composition and conditions are not particularly limited. The description of the nucleoside derivative or a salt thereof of the present invention can be incorporated in the description of the synthesis reagent of the present invention by reference, for example. By the synthesis reagent of the present invention, the polynucleotide of the present invention to be described below can be synthesized, for example.

In the synthesis reagent of the present invention, the nucleoside derivative preferably contains at least one of the phosphoramidite compound or the nucleotide derivative, for example.

The synthesis reagent of the present invention may further contain another reagent for use in synthesis of polynucleotide, for example.

(Method for Producing Polynucleotide)

The method for producing a polynucleotide of the present invention includes, as mentioned above, the step of synthesizing a polynucleotide using a nucleotide derivative or a salt thereof including the nucleoside derivative or a salt thereof of the present invention. The method for producing a polynucleotide of the present invention is characterized by using a nucleotide derivative or a salt thereof including the nucleoside derivative or a salt thereof of the present invention in the synthesis step, and other steps and conditions are not particularly limited. The descriptions of the nucleoside derivative or a salt thereof and the synthesis reagent of the present invention can be incorporated in the method for producing a polynucleotide of the present invention by reference, for example. By the method for producing a polynucleotide of the present invention, the polynucleotide of the present invention to be described below can be produced, for example.

In the method for producing a polynucleotide of the present invention, the synthesis reagent of the present invention may be used as the nucleotide derivative or a salt thereof including the nucleoside derivative or a salt thereof of the present invention.

In the synthesis step, the method for synthesizing the polynucleotide is not particularly limited, and the polynucleotide can be synthesized by a known polynucleotide synthesis method. When the phosphoramidite compound is used as the nucleotide derivative or a salt thereof, the polynucleotide can be synthesized by a phosphoramidite method in the synthesis step.

The method for producing the polynucleotide of the present invention may further include a step of purifying the polynucleotide obtained in the synthesis step, for example. The purification method in the purification step is not particularly limited, and the polynucleotide can be purified by a known purification method such as column chromatography.

(Polynucleotide)

As mentioned above, the polynucleotide of the present invention includes, as a building block, a nucleotide derivative or a salt thereof including the nucleoside derivative or a salt thereof of the present invention. The polynucleotide of the present invention is characterized by including, as a building block, a nucleotide derivative or a salt thereof including the nucleoside derivative or a salt thereof of the present invention, and other composition and conditions are not particularly limited. The descriptions of the nucleoside derivative or a salt thereof, the polynucleotide synthesis reagent, and the method for producing a polynucleotide of the present invention can be incorporated in the description of the polynucleotide of the present invention by reference, for example. With the polynucleotide of the present invention, a binding nucleic acid molecule that binds to a target can be produced, for example, as mentioned below. In the polynucleotide of the present invention, the building block means, for example, a part of the polynucleotide.

The polynucleotide of the present invention has a structure represented by the following chemical formula (6), for example. The description of each substituent can be incorporated in the description of each substituent in the chemical formula (6) by reference, for example.

(6)

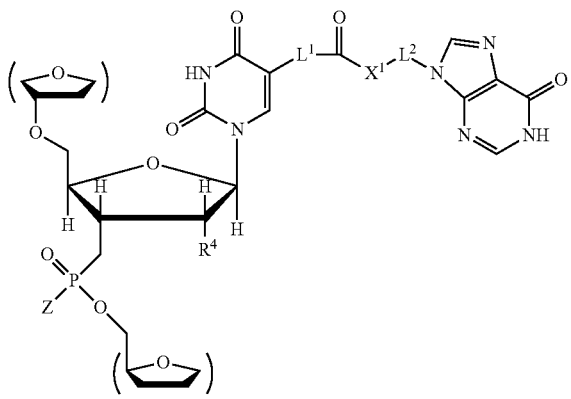

The polynucleotide of the present invention can be, for example, a binding nucleic acid molecule that binds to a target. The target is not particularly limited and can be any target, and as a specific example, the target can be a biomolecule. Examples of the biomolecule include secretory immunoglobulin A (sIgA), an amylase, chromogranin A, β-defensin (Defensin) 2, kallikrein, C-reactive proteins (C-Reactive Protein, CRPs), calprotectin, Statherins, cortisol, and melatonin. The binding nucleic acid molecule can be produced by the method for producing a binding nucleic acid molecule of the present invention to be described below.

The polynucleotide of the present invention may further include, for example, other nucleotide in addition to the nucleotide derivative. Examples of the nucleotide include deoxyribonucleotide and ribonucleotide. Examples of the polynucleotide of the present invention include DNA consisting of deoxyribonucleotide only, DNA/RNA including deoxyribonucleotide and ribonucleotide, and RNA consisting of ribonucleotide only. Other nucleotide may be, for example, a modified nucleotide.

Examples of the modified nucleotide include modified deoxyribonucleotide and modified ribonucleotide. The modified nucleotide can be, for example, a nucleotide with a modified sugar. Examples of the sugar include deoxyribose and ribose. The modified site in the nucleotide is not particularly limited, and may be, for example, the 2'-position or the 4'-position of the sugar. Examples of the modification include methylation, fluorination, amination, and thiation. The modified nucleotide can be, for example, a modified nucleotide with a pyrimidine base (pyrimidine nucleus) as a base or a modified nucleotide with a purine base (purine nucleus) as a base and is preferably the former. Hereinafter, a nucleotide with a pyrimidine base is referred to as pyrimidine nucleotide, the pyrimidine nucleotide modified is referred to as modified pyrimidine nucleotide, a nucleotide with a purine base is referred to as purine nucleotide, and the purine nucleotide modified is referred to as modified purine nucleotide. Examples of the pyrimidine nucleotide include an uracil nucleotide with uracil, cytosine nucleotide with cytosine, and thymine nucleotide with thymine. When the base in the modified nucleotide is a pyrimidine base, it is preferable that the 2'-position and/or the 4'-position of the sugar is modified, for example. Specific examples of the modified nucleotide include modified nucleotides with the 2'-position of the ribose being modified, such as a 2'-methylated-uracil nucleotide, 2'-methylated-cytosine nucleotide, 2'-fluorinated-uracil nucleotide, 2'-fluorinated-cytosine nucleotide, 2'-aminated-uracil nucleotide, 2'-aminated-cytosine nucleotide, 2'-thiated-uracil nucleotide, and 2'-thiated-cytosine nucleotide.

The base in the other nucleotide may be, for example, a natural base (non-artificial base) such as adenine (a), cytosine (c), guanine (g), thymine (t), and uracil (u), or a non-natural base (artificial base). Examples of the artificial base include modified bases and altered bases. The artificial base preferably has the same function as the natural base (a, c, g, t, or u). Example of the artificial base having the same function as the natural base include artificial bases capable of binding to cytosine (c) instead of guanine (g), capable of binding to guanine (g) instead of cytosine (c), capable of binding to thymine (t) or uracil (u) instead of adenine (a), capable of binding to adenine (a) instead of thymine (t), and capable of binding to adenine (a) instead of uracil (u). The modified base is not particularly limited, and may be, for example, a methylated base, a fluorinated base, aminated base, and thiated base. Specific examples of the modified base include 2'-methyluracil, 2'-methylcytosine, 2'-fluorouracil, 2'-fluorocytosine, 2'-aminouracil, 2'-aminocytosine, 2'-thiouracil, and 2'-thiocytosine. In the present invention, for example, the bases represented by a, g, c, t, and u include the meaning of, in addition to the natural bases, the artificial bases having the same functions as the natural bases.

The polynucleotide of the present invention may further include, for example, an artificial nucleic acid monomer in addition to the nucleotide derivative. Examples of the artificial nucleic acid monomer include peptide nucleic acids (PNAs), LNAs, and ENAs. The base in the monomer residue is the same as described above, for example.

The length of the polynucleotide of the present invention is not particularly limited, and the lower limit thereof is, for example, 10-mer, 20-mer, or 25-mer, the upper limit thereof is, for example, 150-mer, 100-mer, or 70-mer, and the range thereof is, for example, 10- to 150-mer, 20- to 100-mer, or 25- to 70-mer.

The polynucleotide of the present invention may further include an additional sequence, for example. Preferably, the additional sequence is bound to at least one of the 5' end or the 3' end, more preferably to the 3' end of the polynucleotide, for example. The additional sequence is not particularly limited, and the length thereof also in not particularly limited.

The polynucleotide of the present invention may further include a labeling substance, for example. Preferably, the labeling substance is bound to at least one of the 5' end or the 3' end, more preferably to the 5' end of the polynucleotide, for example. The labeling substance is not particularly limited, and examples thereof include fluorescent substances, dyes, isotopes, and enzymes. Examples of the fluorescent substances include pyrenes, TAMRA, fluorescein, Cy®3 dyes, Cy®5 dyes, FAM dyes, rhodamine dyes, Texas Red dyes, fluorophores such as JOE, MAX, HEX, and TYE, and examples of the dyes include Alexa dyes such as Alexa®488 and Alexa®647.

The labeling substance may, for example, be linked directly to the nucleic acid molecule or linked indirectly via the additional sequence.

The polynucleotide of the present invention can be used in the state where it is immobilized on a carrier, for example. It is preferable to immobilize either the 5' end or the 3' end, more preferably the 3' end of the polynucleotide of the present invention, for example. When the polynucleotide of the present invention is immobilized, the polynucleotide may be immobilized either directly or indirectly on the carrier, for example. In the latter case, it is preferable to immobilize the nucleic acid molecule via the additional sequence, for example.

(Method for Producing Binding Nucleic Acid Molecule)

The method for producing a binding nucleic acid molecule of the present invention includes, as mentioned above, the steps of: causing a candidate polynucleotide and a target to come into contact with each other; and selecting a candidate polynucleotide bound to the target as a binding nucleic acid molecule that binds to the target, and the candidate polynucleotide is the polynucleotide of the present invention. The method for producing a binding nucleic acid molecule of the present invention is characterized in that the candidate polynucleotide is the polynucleotide of the present invention, for example, and other steps, conditions, etc. are not particularly limited. The descriptions of the nucleoside derivative or a salt thereof, the synthesis reagent, the method for producing polynucleotide, and the polynucleotide can be incorporated in the method for producing a binding nucleic acid molecule of the present invention by reference, for example. In the method for producing a binding nucleic acid molecule of the present invention, the candidate polynucleotide includes, as a building block, a nucleotide derivative or a salt thereof including the nucleoside derivative or a salt thereof of the present invention. Thus, for example, a binding nucleic acid molecule that exhibits excellent binding ability to a target can be produced by the method for producing a binding nucleic acid molecule of the present invention.

As to the method for producing a binding nucleic acid molecule of the present invention, the contact step and the selection step can be performed by the SELEX method, for example.

The number of candidate polynucleotides in the contact step is not particularly limited, and the number of candidate polynucleotides in the contact step is, for example, $4^{20}$ to $4^{120}$ types (about $10^{12}$ to $10^{72}$) and $4^{30}$ to $4^{60}$ types (about $10^{18}$ to $10^{36}$).

In the contact step, a candidate polynucleotide and a target are caused to come into contact with each other. Then, by the contact, the candidate polynucleotide and the target are reacted to form a complex between the candidate polynucleotide and the target. The target to be used in the contact step may be, for example, the target itself or a decomposition product thereof. The conditions under which the candidate polynucleotide and the target are bound are not particularly limited, and for example, the binding can be performed by incubating the both in a solvent for a certain period of time. The solvent is not particularly limited, and for example, a solvent in which the binding of the both is retained is preferable, and specific examples thereof include various buffer solutions.

Next, in the selecting step, a candidate polynucleotide bound to the target is selected as a binding nucleic acid molecule that binds to the target. Specifically, a candidate polynucleotide that forms a complex with the target is collected as the binding nucleic acid molecule. A mixture of the candidate polynucleotide and the target after the contact step contains, in addition to the complex, a candidate polynucleotide that is not involved in formation of the complex, for example. Thus, it is preferable that the complex and unreacted candidate polynucleotide are separated from each other from the mixture, for example. The separation method is not particularly limited and can be, for example, a method utilizing a difference in adsorbability between the target and the candidate polynucleotide or a difference in molecular weight between the complex and the candidate polynucleotide.

In addition to this method, the separation method can be, for example, a method using a target immobilized on a carrier in formation of the complex. That is, the target is immobilized on a carrier in advance to contact between the carrier and the candidate polynucleotide, thereby forming a complex the immobilized target and the candidate polynucleotide. An unreacted candidate polynucleotide that does not bind to the immobilized target is then removed, and the complex between the target and the candidate polynucleotide is dissociated from the carrier. The method for immobilizing the target on a carrier is not particularly limited and can be carried out by a known method. The carrier is not particularly limited, and a known carrier can be used.

In the above-described manner, a binding nucleic acid molecule that binds to a target can be produced.

The method for producing a binding nucleic acid molecule of the present invention may further include, for example, the step of determining a base sequence of the selected binding nucleic acid molecule. The method for determining the base sequence is not particularly limited, and the base sequence can be determined by a known base sequence determination method.

In the method for producing a binding nucleic acid molecule of the present invention, for example, one set of the contact step and the selection step may be performed for two or more cycles in total, and a specific example thereof is 3 to 15 cycles.

EXAMPLES

The present invention is described more specifically below with reference to examples. It is to be noted, however, that the scope of the present invention is not limited by these examples. Commercially available reagents in the examples were used in accordance with their protocols, unless otherwise stated.

Example 1

IA8 was prepared by the following synthesis examples.

Electrospray ionization mass spectrometry (ESI-MS) was performed using a mass spectrometer (API2000, vendor: Applied Biosystems) in positive or negative ion mode. $^1$H NMR spectra were obtained using a nuclear magnetic resonance instrument (JNM-ECS400, manufactured by JEOL). Chemical shifts are expressed as relative δ (ppm) to the internal standard, tetramethylsilane (Me$_4$Si). Ion-exchange chromatography was performed using a chromatographic system (ECONO system, manufactured by Bio-Rad). In the ion-exchange chromatography, a glass column (φ25×500 mm) packed with diethylaminoethyl (DEAE) A-25-Sephadex (manufactured by Amershambiosciences) was used.

(Synthesis Example 1) Synthesis of TB4

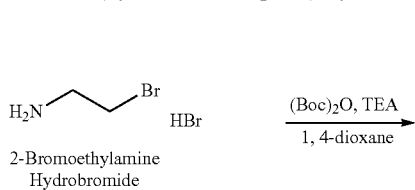

2-Bromoethylamine Hydrobromide

-continued

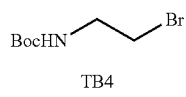

TB4

2-Bromethylamine Hydrobromide (501 mg, 2.28 mmol) was weighed and suspended in 1,4-dioxan (5 ml), and the thus-obtained mixture was then stirred for 30 minutes under an ice bath. To the thus-obtained mixture, Di-tert-butyl dicarbonate (558 mg, 2.56 mmol, 1.1 eq.) was added, and triethylamine (318 μL, 2.28 mmol, 1 eq.) was added dropwise. The mixture was then stirred for 30 minutes under the ice bath as it was and stirred for 48 hours at room temperature. A precipitate was removed by suction filtration, and a filtrate was collected. The filtrate was dissolved in dichloromethane, and the thus-obtained solution was then subjected to separation twice with distilled water. A magnesium sulfate was added to an organic phase, and the thus-obtained mixture was subjected to filtration. The solvent was distilled off from the filtrate under reduced pressure to give liquid TB4. Physical properties of TB4 are shown below. Yield amount: 0.443 g, Yield: 86.7%

ESI-MS (positive ion mode) m/z, found=223.2, calculated for $[(M+H)^+]$=223.0.

$^1$HNMR (400 MHz, CDCl$_3$) δ7.27 (1H, s) 3.53 (2H, t) 3.46 (2H, t) 1.45 (9H, s)

(Synthesis Example 2) Synthesis of IA1

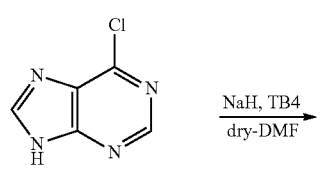

6-chloropurine

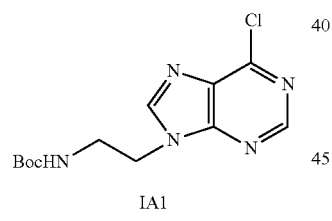

IA1

The atmosphere of 6-chloropurine (107 mg, 692 μmol) was replaced with Ar, and the 6-chloropurine was suspended in dry-DMF, and the thus-obtained mixture was stirred for 30 minutes under an ice bath. NaH (32 mg, 1.31 mmol, 1.9 eq.) was added to the thus-obtained mixture, and the mixture was then stirred for 2 hours under ice cooling. TB4 (352 mg, 1.57 mmol, 2.2 eq.) dissolved in dry-DMF was thereafter added to the mixture, which was then stirred at room temperature. After the reaction, the solvent was distilled off. The residue was suspended in chloroform, and a filtrate was collected. The collected filtrate was subjected to separation with water, and an organic phase was purified by column chromatography, to give IA1. Physical properties of IA1 are shown below.

Yield amount: 108 mg, Yield: 52.4%

ESI-MS (positive ion mode) m/z, found=296.2, calculated for $[(M+H)^+]$=296.1.

$^1$HNMR (400 MHz, CDCl$_3$) δ8.75 (1H, s) 8.10 (1H, s) 4.47 (2H, t) 3.60 (2H, q) 1.39 (9H, s)

(Synthesis Example 3) Synthesis of IA2

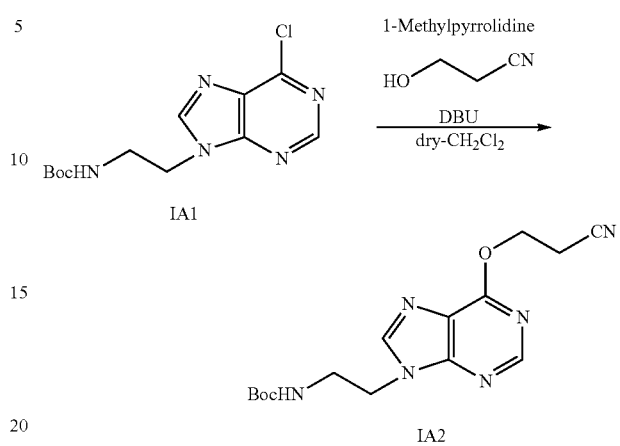

The atmosphere of IA1 (130 mg, 4.38×10$^{-4}$ mol) was replaced with Ar, and the IA1 was then suspended in dry-CH$_2$Cl$_2$ (1.5 ml), and the thus-obtained mixture was stirred for 30 minutes under an ice bath. 1-Methylpyrrolidine (126 μL, 1.21 mmol, 3 eq.) was thereafter added to the mixture, which was then further stirred for 30 minutes under the ice bath. Ethylene Cyanohydrin (90 μL, 1.32 mmol, 3 eq.) and DBU (29 μL, 1.94×10$^{-4}$ mol, 0.46 eq.) were added to the mixture to react under the ice bath. After the reaction, the mixture was subjected to separation twice with water, and an organic phase was purified by column chromatography, to give IA2. Physical properties of IA2 are shown below.

Yield amount: 78 mg, Yield: 53%

ESI-MS (positive ion mode) m/z, found=333.1, calculated for $[(M+H)^+]$=333.2.

found=355.3, calculated for $[(M+Na)^+]$=355.2.

$^1$HNMR (400 MHz, CDCl$_3$) δ8.53 (1H, s), 7.94 (1H, s), 4.85 (2H, t), 4.43 (2H, t), 3.59 (2H, q), 3.00 (2H, t), 1.41 (1H, s)

(Synthesis Example 4) Synthesis of IA3

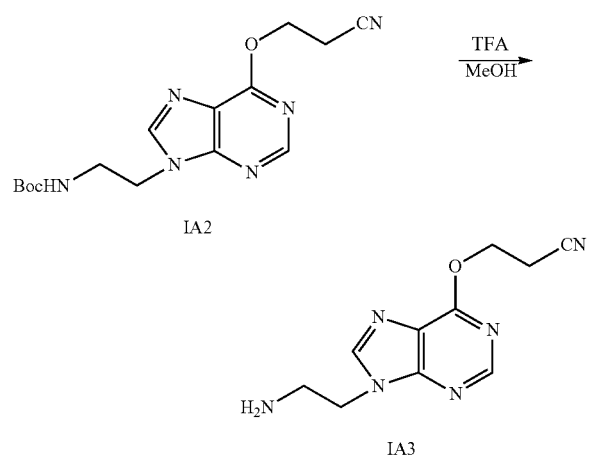

IA2 (118 mg, 3.55 mmol) was dissolved in methanol (1 ml), and Trifluoroacetate (5 ml) was then added to the thus-obtained solution dropwise to react at room temperature. After the reaction, the solvent was distilled off, the residue was suspended in diethyl ether, and the thus-obtained mixture was then subjected to filtration. The residue was collected to give IA3. Physical properties of IA3 are shown below.

Yield amount: 128 mg, Yield: 104.1%

ESI-MS (positive ion mode) m/z, found=233.1, calculated for [(M+H)$^+$]=233.2.

found=255.2, calculated for [(M+Na)$^+$]=255.2.

found=271.2, calculated for [(M+K)$^+$]=271.2.

$^1$HNMR (400 MHz, DMSO-d$_6$) δ8.68 (1H, s), 8.49 (1H, s), 4.84 (2H, t), 4.60 (2H, t), 3.24 (2H, t)

(Synthesis Example 5) Synthesis of IA4 residue was collected to give IA4. Physical properties of IA4 are shown below.

Yield amount: 84 mg, Yield: 49.7%

ESI-MS (positive ion mode) m/z, found=513.1, calculated for [(M+H)$^+$]=513.2, found=535.2, calculated for [(M+Na)$^+$]=535.2, found=551.1, calculated for [(M+K)$^+$]=551.2, ESI-MS (negative ion mode) m/z, found=511.3, calculated for [(M−H)$^-$]=511.2

$^1$HNMR (400 MHz, DMSO-d$_6$) δ8.51 (1H, s), 8.30 (1H, s), 8.22 (1H, s), 7.05 (1H, d), 6.89 (1H, d), 6.11 (1H, t), 5.25 (2H, d), 5.13 (1H, t), 4.70 (2H, t), 4.32 (2H, t), 3.77 (1H, d), 3.58 (2H, m), 3.11 (2H, t), 2.12 (2H, m)

(Synthesis Example 6) Synthesis of IA5

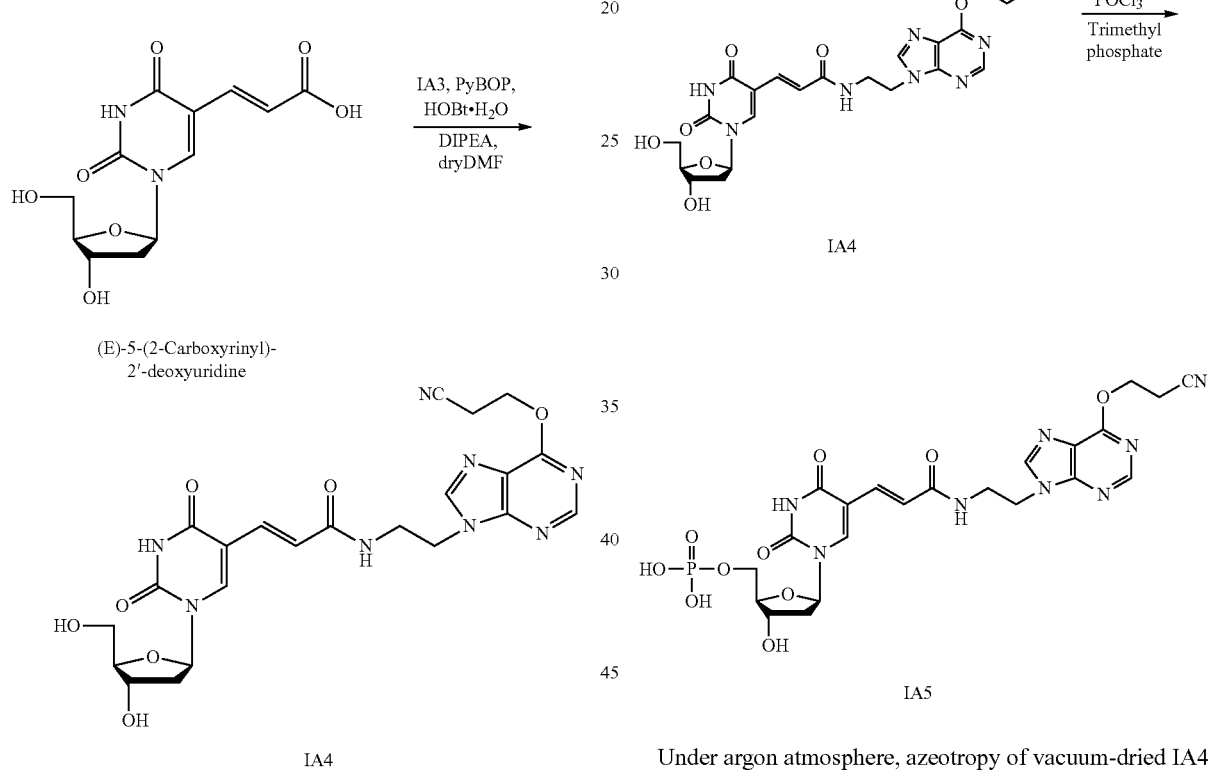

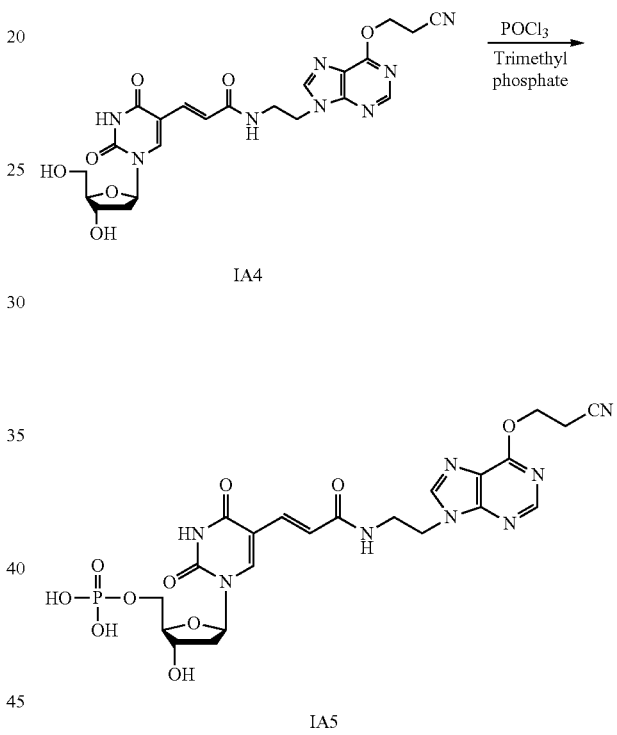

The atmosphere of (E)-5-(2-Carboxyrinyl)-2'-deoxyuridine (98 mg, 3.29×10$^{-4}$ mol) was replaced with Ar, and HOBt.H$_2$O (69 mg, 4.51×10$^{-4}$ mol, 1.3 eq.) and PyBOP (223 mg, 4.42×10$^{-4}$ mol, 1.3 eq.) were added thereto. The thus-obtained mixture was then dissolved in dry-DMF (1 ml), and DIPEA (1.18 ml, 6.61 mmol, 20 eq.) was then added to the thus-obtained solution. This solution was then added dropwise to IA3 (128 mg, 3.70×10$^{-4}$ mol, 1.1 eq.) the atmosphere of which had been replaced with Ar and which had then been dissolved in dry-DMF (0.5 ml), to react at room temperature. After the reaction, the solvent was distilled off, the residue was suspended in CDCl$_3$, and the mixture was then subjected to sonication and filtration. The residue was collected and suspended in MeOH, and the mixture was then subjected to sonication and filtration. The Under argon atmosphere, azeotropy of vacuum-dried IA4 (80 mg, 1.56×10$^{-4}$ mol) and dry-DMF (20 ml) was caused twice, and azeotropy of the IA4 and dry-MeCN (10 ml) was caused three times. The thus-obtained azeotrope was suspended in dry-Trimetyl phosphate (30 ml), and Phosphoryl chloride (620 μL, 6.65×10$^{-4}$ mol, 42.6 eq.) was added dropwise to the thus-obtained mixture under an ice bath, and the mixture was then stirred for 19 hours. Thereafter, a 1 mol/L TEAB buffer was added to the mixture, which was then stirred for 15 minutes. Then, the solvent was distilled off under reduced pressure, crystallization was performed in Ether and MeCN, and filtration was performed to obtain a yellow precipitate. This yellow precipitate was dissolved in water, purified by anion-exchange column chromatography, and freeze-dried, to give IG5. Physical properties of IA5 are shown below.

Yield amount: 57.96 μmol, Yield: 37%

ESI-MS (negative ion mode) m/z, found=590.9, calculated for [(M−H)$^-$]=591.1

(Synthesis Example 7) Synthesis of IA6

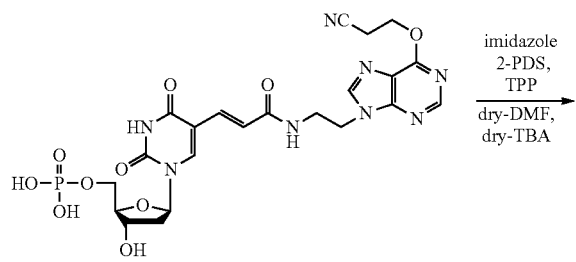

IA5

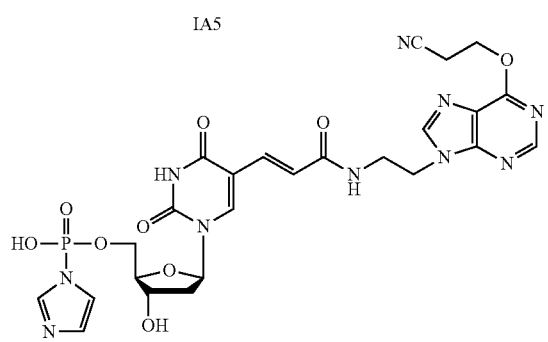

IA6

Azeotropy of vacuum-dried IA5 (57.96 μmol) and dry-Pyridine (5 ml) was caused three times, and the thus-obtained azeotrope was then vacuum-dried over night. The atmosphere of the azeotrope was replaced with Ar, the azeotrope was then dissolved in dry-DMF (2 ml) and dry-TEA (55 μL, $3.95 \times 10^{-4}$ mol, 6.8 eq.), and Imidazole (26 mg, $3.82 \times 10^{-4}$ mol, 6.6 eq.), 2,2'-Dithiodipyridine (24 mg, $1.09 \times 10^{-4}$ mol, 1.9 eq.), and Triphenylphosphine (30 mg, $1.37 \times 10^{-4}$ mol, 2 eq.) were added to the thus-obtained solution, which was then stirred at room temperature. After 9 hours of the stirring, the thus-obtained reaction solution was added to a solution obtained by dissolving Sodium perchlorate (86 mg, $7.02 \times 10^{-4}$ mol, 12 eq.) in dry-Acetone (18 ml), dry-Ether (27 ml), and dry-TEA (2 ml), then stood still for 30 minutes at 4° C., and subjected to decantation with dry-Ether (12 ml) twice to obtain a precipitate. This precipitate was vacuum-dried to give IA6 as a crude. Physical properties of IA6 are shown below.

Theoretical yield amount: 57.96 μmol

ESI-MS (negative ion mode) m/z, found=641.3, calculated for $[(M-H)^-]$=641.2

(Synthesis Example 8) Synthesis of IA7

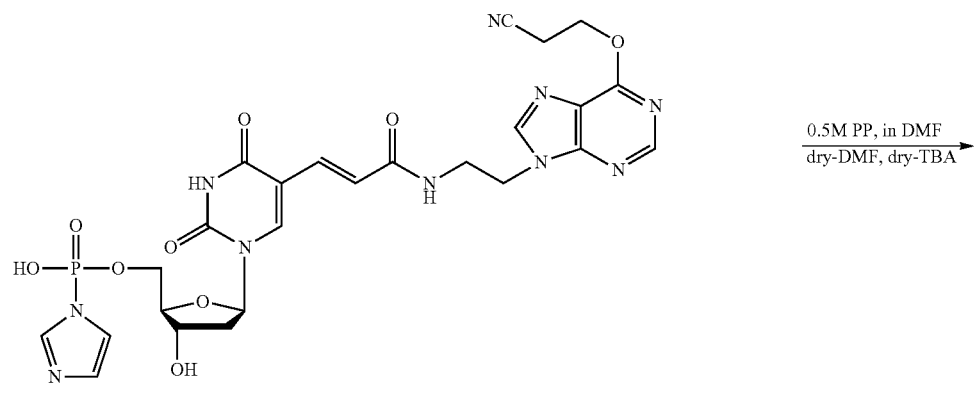

IA6

-continued

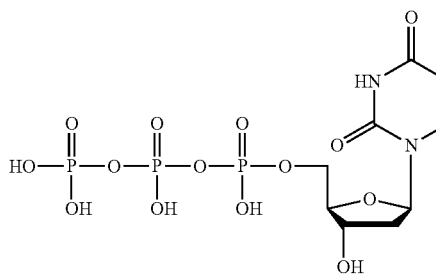

IA7

The atmosphere of the vacuum-dried IA6 (57.96 μmol) was replaced with Ar, an azeotropy of the IA6 and dry-Pyridine (5 ml) was caused twice, and the thus-obtained azeotrope was then suspended in dry-DMF (1 ml). Dry-n-Tributylamine (55 μL, $2.30 \times 10^{-4}$ mol, 4 eq.) and 0.5 mol/L n-Tributylamine pyrophosphate in DMF (0.6 ml, $2.96 \times 10^{-4}$ mol, 5 eq.) were added to the thus-obtained mixture, which was then stirred at room temperature. After 12 hours of the stirring, a 1 mol/L TEAB buffer (5 ml) was added to the mixture, which was then stirred for 30 minutes, and a solvent was thereafter distilled off under reduced pressure. Water was added, an aqueous layer was separated with Ether twice, purified by anion-exchange column chromatography, and freeze-dried, to give IA7. Physical properties of IA7 are shown below.

Crude yield amount: 16.65 μmol, Yield: 28.7%

ESI-MS (negative ion mode) m/z, found=751.0, calculated for $[(M-H)^-]$=751.1

(Synthesis Example 9) Synthesis of IA8

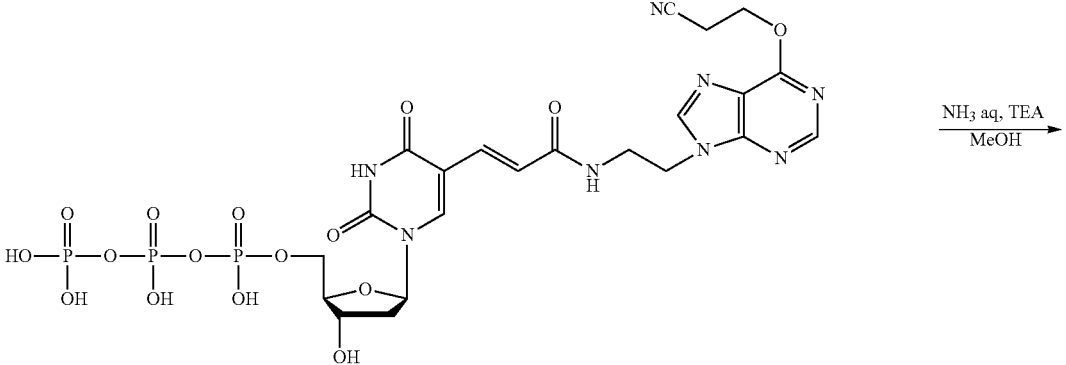

IA7

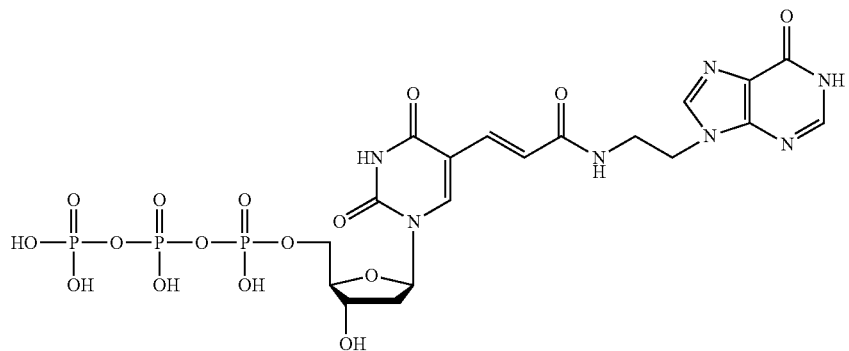

IA8

The IA7 (12.49 μmol) was dissolved in MeOH (500 μL), 28% NH₃ (1500 μL) and triethylamine (300 μL) were added to the thus-obtained solution, which was then reacted for 1.5 hours at room temperature. After the reaction, the solvent was distilled off under reduced pressure, and a residue was freeze-dried to give IA8. Physical properties of IA8 are shown below.

Yield amount: 8.39 μmol, Yield: 67.2%

ESI-MS (negative ion mode) m/z, found=697.9, calculated for [(M−H)⁻]=699.1

Example 2

The present example examined whether binding nucleic acid molecules that bind to sIgA and binding nucleic acid molecules that bind to amylase can be obtained using IA8.

(1) Binding Nucleic Acid Molecule

Binding nucleic acid molecules that bind to the respective targets were obtained by the SELEX method, except that candidate polynucleotides prepared by using, in addition to deoxyribonucleotides containing adenine, guanine, and cytosine, respectively (dATP, dGTP, and dCTP, respectively), IA8 as deoxyribonucleotide were used. Specifically, the binding nucleic acid molecules were obtained in the following manner. sIgA (manufactured by MP Biomedicals, LLC-Cappel Products) or human salivary amylase (manufactured by Lee BioSolutions, Inc.) as the target was bound to beads (Dynabeads MyOne Carboxylic Acid, manufactured by Invitrogen) according to the protocols attached to the products. After binding the target, the beads were washed with a selection buffer (SB Buffer: 40 mmol/L HEPES, 125 mmol/L NaCl, 5 mmol/L KCl, 1 mmol/L MgCl₂, 0.01% Tween 20®, pH 7.5), whereby target beads were prepared. dsDNAs with IA8 inserted therein were prepared using complementary strands with their 5' ends modified with biotin (forward (Fw) primer region-N30 (30 bases)-reverse (Rv) primer region), forward primers and DNA polymerase (KOD Dash, Toyobo Co., Ltd.), and dATP, dGTP, dCTP, and IA8. Subsequently, the dsDNAs were bound to the beads (Dynabeads MyOne Carboxylic Acid), and then, ss (single strand) DNAs were eluted with a 0.02 mol/L NaOH aqueous solution. Furthermore, the NaOH aqueous solution was neutralized with a 0.08 mol/L hydrochloric acid aqueous solution. Thus, an ssDNA library was prepared. 20 pmol of the library was mixed with 250 μg of the target beads at 25° C. for 15 minutes. Then, the ssDNAs bound to the beads were eluted with a 7 mol/L urea aqueous solution. The eluted ssDNAs were amplified by PCR using the forward primers and the biotin-modified reverse primers. In the PCR, dATP, thymine-containing deoxyribonucleotide (dTTP), dGTP, and dCTP were used as deoxyribonucleotides. The obtained dsDNAs were bound to magnetic beads (Dynabeads MyOne SA C1 magnetic beads, manufactured by Invitrogen). Thereafter, forward strands were eluted with a 0.02 mol/L NaOH aqueous solution and removed. After removing the forward strands, the magnetic beads were washed with the SB buffer. Using the magnetic beads with the complementary strands immobilized thereon, forward primers and DNA polymerase (KOD Dash, Toyobo Co., Ltd.), dATP, dGTP, dCTP, and IA8, dsDNAs with IA8 inserted therein were prepared in the above-described manner. Next, an ssDNA library was prepared by eluting forward strands with a 0.02 mol/L NaOH aqueous solution, and this library was used in a subsequent round. Nucleic acid molecules that bind to sIgA or amylase were selected by performing eight rounds of the same process. Thereafter, PCR was performed using forward primers and reverse primers without biotin modification.

The obtained nucleic acid molecules were subjected to sequencing using a sequencer (GS junior sequencer, Roche).

As a result, a binding nucleic acid molecule consisting of the base sequence of SEQ ID NO: 1 below was obtained as the binding nucleic acid molecule that binds to amylase, and a binding nucleic acid molecule consisting of the base sequence of SEQ ID NO: 2 below was obtained as the binding nucleic acid molecule that binds to sIgA. In the base sequences of SEQ ID NOs: 1 and 2, the underlined bases T are IA8.

```
α-amylase-binding nucleic acid molecule
                                      (SEQ ID NO: 1)
5'-GGAATCAGTCCGCCGCTAATACGCTGGTATGGTTGAAGTGCGTATTA
GACATGTGAACGATCCTGTGCCCGATAAAG-3' sIgA-binding nucleic acid molecule
                                      (SEQ ID NO: 2)
5'-GGAATCAGTCCGCCGCTAATACTAGTCATCGCTTTTAATTTCGCATT
GTACCGTGAACGATCCTGTGCCCGATAAAG-3'
```

(2) Examination of Binding by Surface Plasmon Resonance (SPR)

The binding between the amylase-binding nucleic acid molecule and amylase and the binding between the sIgA-binding nucleic acid molecule and sIgA were measured under the following SPR conditions. The amylase-binding nucleic acid molecule and the sIgA-binding nucleic acid molecule adapted so that a 20-mer poly(dT) was added to the 3' ends were each used as the following ligand 2. Further, as a control, examination of the binding was performed in the same manner except that, in a system examining the binding of the amylase-binding nucleic acid molecule, the sIgA, chromogranin A (CgA, Creative BioMart), and bovine serum albumin (BSA) were used as the following analytes, and in a system examining the binding of the sIgA-binding nucleic acid molecule, the amylase, CgA, and BSA were used as the following analytes.

(SPR Measurement Conditions)
Measurement device: ProteOn™ XPR36 (BioRad)
Measurement chip: ProteOn™ NLC Sensor Chip (manufactured by BioRad)
Ligand 1: poly(dT) (20-mer) with the 5' end thereof being modified with biotin: 5 μmol/L
Buffer: 40 mmol/L HEPES, 125 mmol/L NaCl, 1 mmol/L MgCl₂, 5 mmol/L KCl, 0.01%
Tween® 20, pH 7.4
Ligand 2: buffer containing a binding nucleic acid molecule with poly(A) (20-mer) added to the 3' end at 200 nmol/L
Ligand flow rate: 25 μL/min, 80 sec
Analyte: buffer containing a target at 400 nmol/L
Analyte Flow Rate: 50 μL/min
Contact Time: 120 sec
Dissociation: 300 sec
  Amylase: α-amylase (manufactured by Lee Biosolutions, Catalogue number: #120-10)
  sIgA: IgA (Secretory), Human (manufactured by MP Biomedicals, LLC-Cappel Products, Catalogue number: #55905)
  CgA: recombinant full length Human Chromogranin A (manufactured by Creative BioMart, Catalog number: #CHGA 26904TH)
  BSA: Bovine Serum Albumin (manufactured by SIGMA, Catalogue number: #A7906)

After injection of the ligand 2, signal intensity (RU) measurement was performed. With 0 seconds being the start of the injection of the ligand 2, the mean value ($RU_{115-125}$) of signal intensities from 115 seconds to 125 seconds was determined. Then, a ratio ($RU_{115-125}/RU_{immob}$) between the RU value ($RU_{immob}$) at the time when the poly(dT)-added aptamer is bound to the biotinylated poly(dA) and $RU_{115-125}$ was calculated.

Figure 1B:
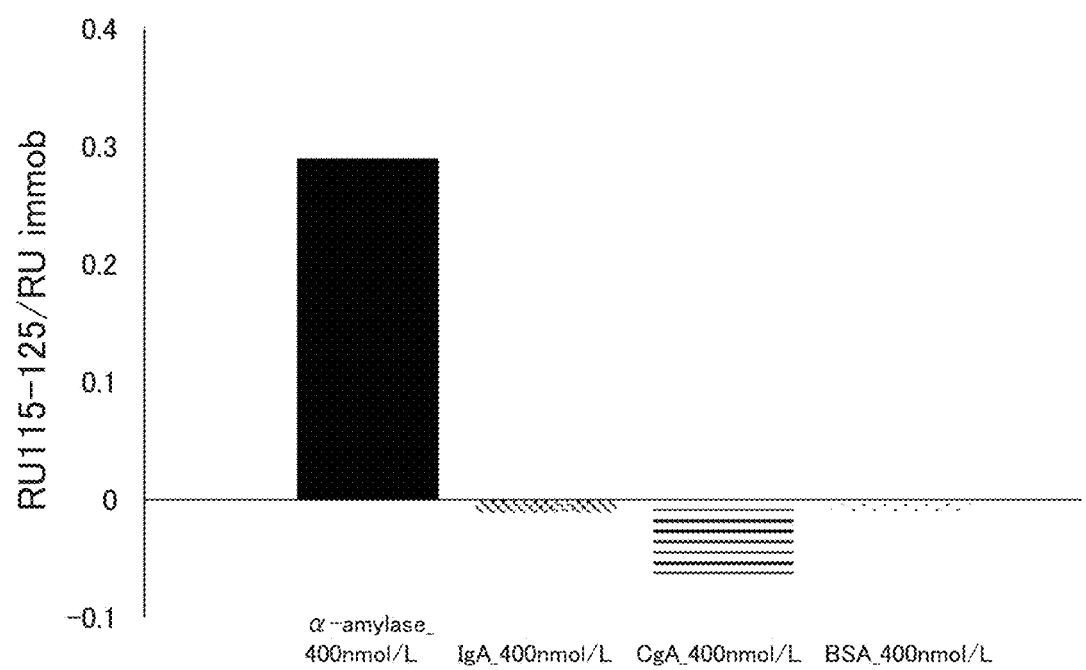

FIGS. 1A and 1B are graphs illustrating the binding ability of the amylase-binding nucleic acid molecule to the amylase. In FIG. 1A, the horizontal axis indicates the time elapsed after the injection of the ligand, and the vertical axis indicates the relative value (RU) of the binding force. In FIG. 1B, the horizontal axis indicates the type of the analyte, and the vertical axis indicates $RU_{115-125}/RU_{immob}$. As can be seen in FIGS. 1A and 1B, the amylase-binding nucleic acid molecule bound to the amylase whereas it did not bind to any control.

Figure 2A:
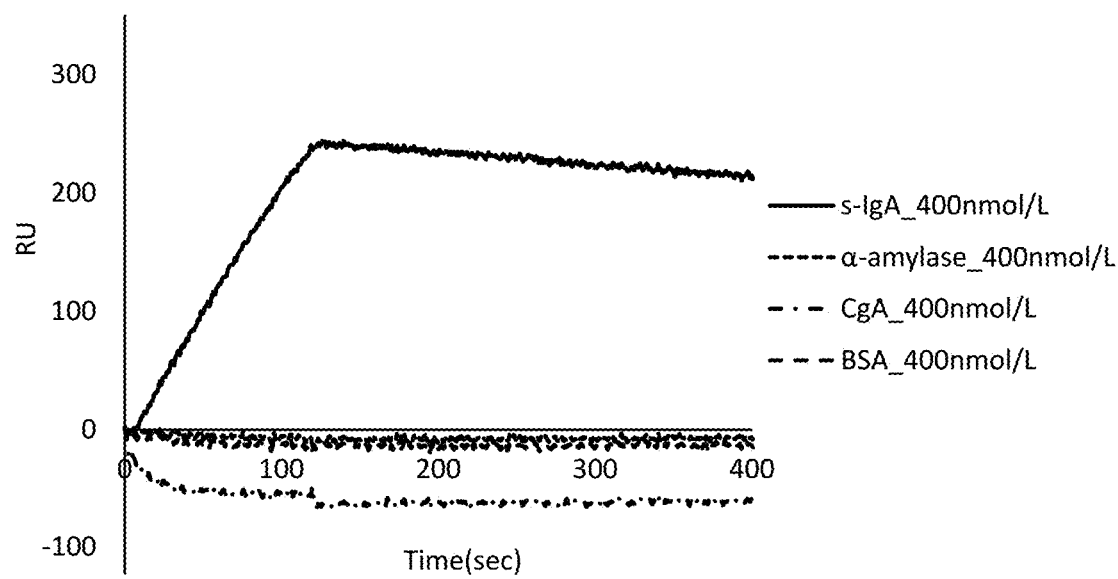
FIGS. 2A and 2B are graphs illustrating the binding ability of the secretory immunoglobulin A (sIgA)-binding nucleic acid molecule to sIgA in Example 2.
Figure 2B:
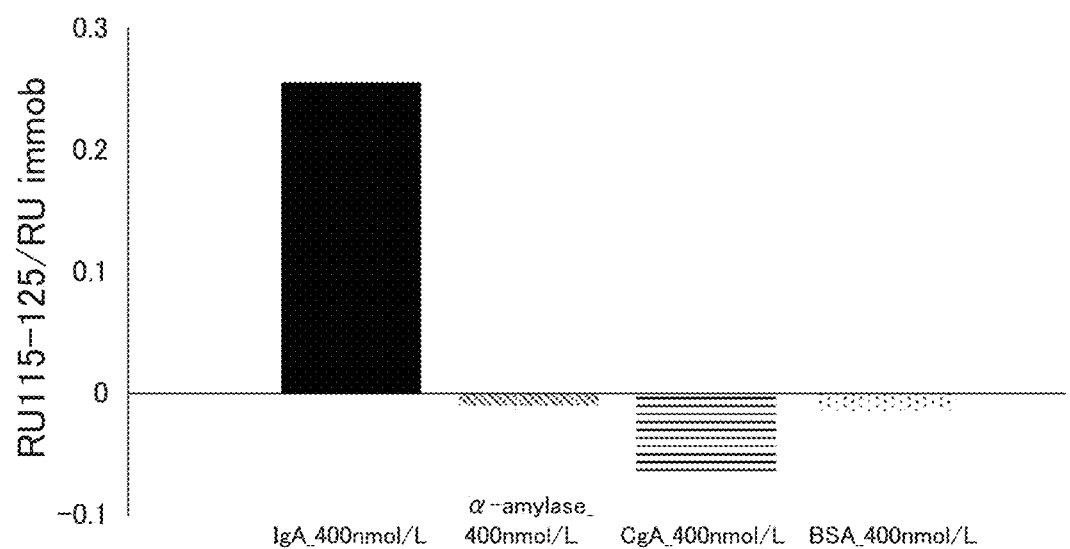

FIGS. 2A and 2B are graphs illustrating the binding ability of the sIgA-binding nucleic acid molecule to sIgA. In FIG. 2A, the horizontal axis indicates the time elapsed after the injection of the ligand, and the vertical axis indicates the relative value (RU) of the binding force. In FIG. 2B, the horizontal axis indicates the type of the analyte, and the vertical axis indicates $RU_{115-125}/RU_{immob}$. As can be seen in FIGS. 2A and 2B, the sIgA-binding nucleic acid molecules bound to sIgA whereas it did not bind to any control.

From these results, it was found that a binding nucleic acid molecule that binds to amylase and a binding nucleic acid molecule that binds to sIgA can be obtained using IA8, which is the nucleoside derivative of the present invention.

(3) Examination of Binding Force

The relative value (RU) of the binding force was measured in the same manner as in the above item (2), except that the amylase-binding nucleic acid molecule having a 20-mer poly(T) added to its 3' end was used as the ligand 2 and that the concentration of the α-amylase as the analyte was set to 12.5, 25, 50, 100, or 200 nmol/L. Also, the relative value (RU) of the binding force was measured in the same manner as in the above item (2), except that the sIgA-binding nucleic acid molecule having a 20-mer poly(T) added to its 3' end was used as the ligand 2 and that the concentration of sIgA as the analyte was 12.5, 25, 50, 100, or 200 nmol/L.

Figure 3:
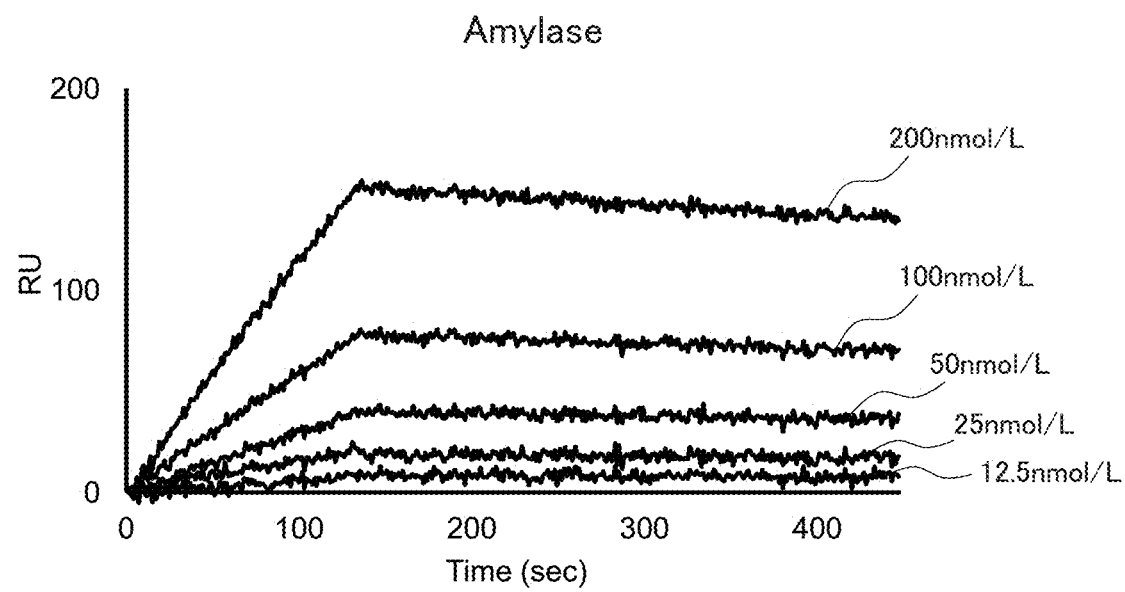
FIG. 3 is a graph illustrating the binding ability of the amylase-binding nucleic acid molecule to amylase in Example 2.
Figure 4:
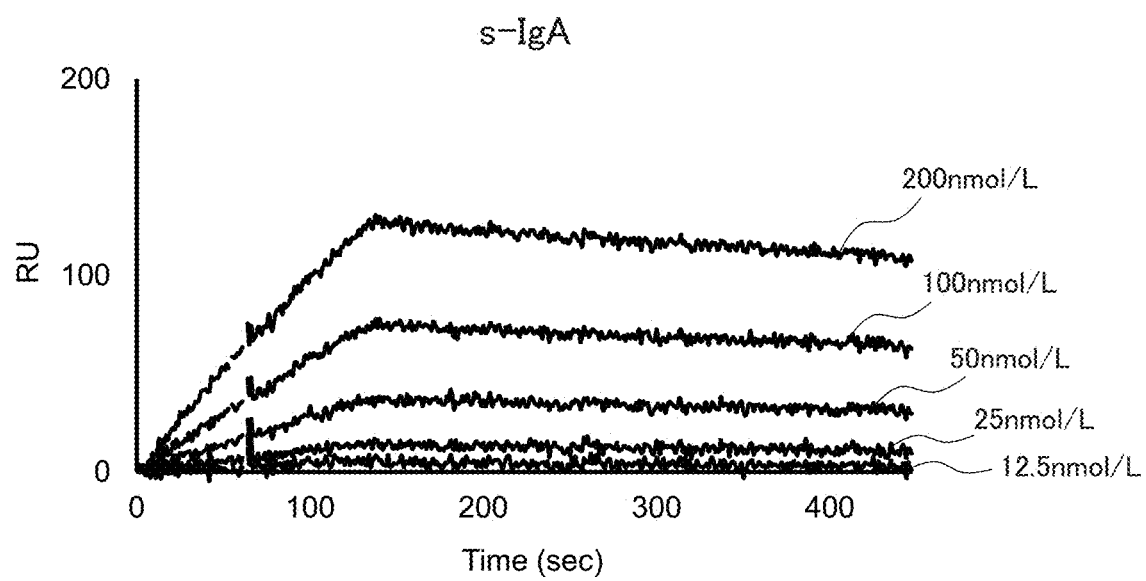
FIG. 4 is a graph illustrating the binding ability of the secretory immunoglobulin A (sIgA)-binding nucleic acid molecule to sIgA in Example 2.

FIG. 3 is a graph showing the binding ability of the amylase-binding nucleic acid molecule to the amylase. FIG. 4 is a graph showing the binding ability of the sIgA-binding nucleic acid molecule to sIgA. In each of FIGS. 3 and 4, the horizontal axis indicates the time elapsed after the injection of the ligand, and the vertical axis indicates the relative value (RU) of the binding force. As shown in FIG. 3, for the amylase-binding nucleic acid molecule, the signal intensity was increased as the concentration of amylase was increased. Moreover, as shown in FIG. 4, for the sIgA-binding nucleic acid molecule, the signal intensity was increased as the concentration of sIgA was increased.

Then, based on the relative values (RU) of the binding force measured in the above, the dissociation constant between the amylase-binding nucleic acid molecule and the α-amylase and the dissociation constant between the sIgA-binding nucleic acid molecule and sIgA were calculated. As a result, the dissociation constant between the amylase-binding nucleic acid molecule and the amylase was 38.6 nM, and the dissociation constant between the sIgA-binding nucleic acid molecule and sIgA was 3.61 nM. These results demonstrate that both the binding nucleic acid molecules have excellent binding ability to the targets.

(4) Examination of Binding by Capillary Electrophoresis

Binding between the amylase-binding nucleic acid molecule and amylase was measured by capillary electrophoresis performed under the following conditions. The amylase-binding nucleic acid molecule adapted so that it was labeled with a fluorescence dye included in the kit was used. As controls, the measurement was performed in the same manner except that amylase was not added as the target.

Figure 5:
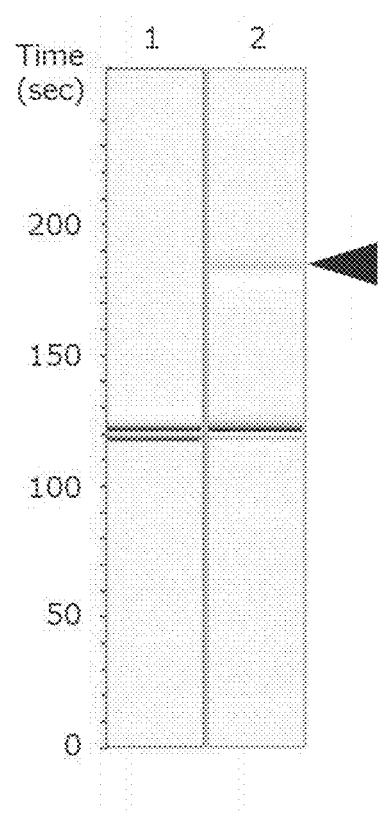
FIG. 5 is a photograph illustrating the result of capillary electrophoresis in Example 2.

(Conditions of Capillary Electrophoresis)
Measurement device: Cosmo-i SV1210 (Hitachi High-Technologies Corporation)
Measurement chip: i-chip 12 (Hitachi Chemical Company, Ltd.)
Electrophoresis gel: 0.6% (Hydroxypropyl)methyl cellulose, viscosity 2. 600-5, 600 (manufactured by SIGMA, Catalogue number: #H7509)
Gel dissolving buffer: 40 mmol/L HEPES (pH 7.5), 5 mmol/L KCl, 1 mmol/L $MgCl_2$
Clone: solution containing 600 nmol/L amylase-binding nucleic acid molecule labeled with a fluorescent dye included in the kit, 40 mmol/L HEPES (pH 7.5), 125 mmol/L NaCl, 5 mmol/L KCl, and 1 mmol/L $MgCl_2$
Target: solution containing 5.9 μmol/L amylase (α-Amylase-High Purity, Human, manufactured by Lee BioSolutions, Inc., Catalogue number: #120-10), 40 mmol/L HEPES (pH 7.5), 125 mmol/L NaCl, 5 mmol/L KCl, and 1 mmol/L $MgCl_2$
Folding: 95° C., after 5 min, on ice 5 min
Mixing: after addition of target, room temperature (around 25° C.), 30 min, 1000 rpm
Injection voltage: 300 V
Injection time: 120 sec
Separation voltage: 350 V
Separation Time: 260 sec The result obtained is shown in FIG. 5. FIG. 5 is a photograph illustrating the result of capillary electrophoresis. In FIG. 5, the electrophoresis time is shown on the left side of the photograph, and the respective lanes show, from the left, the result obtained regarding the control (without amylase) and the result obtained when the amylase was used. As can be seen in FIG. 5, the electrophoresis time in the presence of the amylase was longer than that in the control without amylase. From this result, it was found that the amylase-binding nucleic acid molecule binds to amylase.

Comparative Example

Comparative Example examined that a binding nucleic acid molecule that binds to amylase cannot be obtained using only a natural base. Unless otherwise stated, an operation was performed in the same manner as in Example 2.

Candidate polynucleotides were synthesized using the respective deoxyribonucleotides containing adenine, guanine, cytosine, and thymine (dATP, dGTP, dCTP, and dTTP, respectively), and the SELEX method was performed. Then, binding of each of obtained binding nucleic acid molecules to amylase was examined by SPR. The sequences of the nucleic acid molecules are shown below.

```
A ML2196R8m4
                                          (SEQ ID NO: 3)
GGTAAGACTCCCGCCAGATTTGGGTGGGGGCGGGGGTGGAGGAGGTGGC
GGTGAAGCCCTCGGTCGAAATC

A ML1217R8m4
                                          (SEQ ID NO: 4)
GGAAACCCTGCGTCCTGAAATTGCGCTGCGATAGTGAAGGCATAACAGGT
TCACTCATCTGTGCTGGCGGAATAG
```

Figure 6:
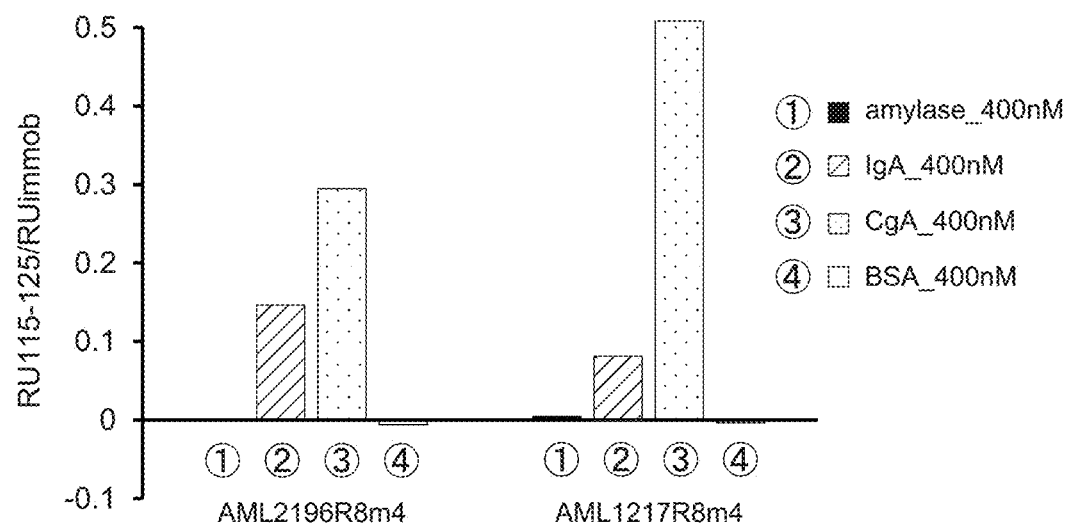
FIG. 6 shows graphs illustrating the binding ability of the binding nucleic acid molecule to amylase in Comparative Example.

The results obtained are shown in FIG. 6. FIG. 6 shows graphs illustrating the binding ability of each binding nucleic acid molecule to amylase. The horizontal axis indicates the kind of each binding nucleic acid molecule, and the vertical axis indicates $RU_{115-125}/RU_{immob}$. In each graph, the respective results are, from the left, the result obtained using amylase, the result obtained using sIgA, the result obtained using CgA, and the result obtained using BSA. In FIG. 6, the binding force ($RU_{115-125}/RU_{immob}$) of each of the obtained nucleic acid molecules to amylase was about 0. In addition, a cross reaction of binding to a substance(s) other than the target was also determined.

From these results, it was found that any binding nucleic acid molecule that binds to amylase cannot be obtained using only a natural base.

Although the present invention is described above with reference to embodiments and examples, the present invention is not limited thereto. Various modifications can be made within the scope of the present invention which can be understood by those skilled in the art.

The present application is based upon and claims the benefit of priority from Japanese patent application No. 2016-230196, filed on Nov. 28, 2016, and the entire disclosure of which is incorporated herein its entirety by reference.

INDUSTRIAL APPLICABILITY

The present invention can provide a novel nucleoside derivative or a salt thereof. The nucleoside derivative of the present invention has two of a purine ring-like structure and a pyrimidine ring-like structure. The nucleoside derivative of the present invention thus has, for example, a relatively larger number of atoms capable of interacting within or between molecules than a nucleoside derivative having one purine ring-like structure or one pyrimidine ring-like structure. The binding nucleic acid molecule including the nucleoside derivative of the present invention therefore has an improved binding ability to a target, for example, compared to a nucleoside derivative having one purine ring-like structure or one pyrimidine ring-like structure. Thus, with the nucleoside derivative of the present invention, a binding nucleic acid molecule that exhibits excellent binding ability to a target can be produced, for example. Accordingly, the present invention is really useful, for example, in the fields of analysis, medicine, life science, and the like.

[Sequence Listing] TF16098WO_ST25.txt

The invention claimed is:

1. A nucleoside derivative or a salt thereof, represented by the following chemical formula 1:

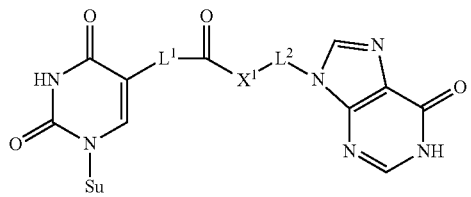

where in the chemical formula 1,
Su is an atomic group having a sugar skeleton at a nucleoside residue or an atomic group having a sugar phosphate skeleton at a nucleotide residue, and may or may not have a protecting group,
$L^1$ and $L^2$ are each independently a straight-chain or branched, saturated or unsaturated hydrocarbon group having 2 to 10 carbon atoms,
$X^1$ is an imino group (—$NR^1$—), an ether group (—O—), or a thioether group (—S—), and
$R^1$ is a hydrogen atom or a straight-chain or branched, saturated or unsaturated hydrocarbon group having 2 to 10 carbon atoms.

2. The nucleoside derivative or a salt thereof according to claim 1, wherein the $X^1$ is an imino group (—$NR^1$—).

3. The nucleoside derivative or a salt thereof according to claim 1, wherein the $L^1$ is a vinylene group (—CH=CH—).

4. The nucleoside derivative or a salt thereof according to claim 1, wherein the $L^2$ is an ethylene group (—$CH_2$—$CH_2$—).

5. The nucleoside derivative or a salt thereof according to claim 1, wherein the $R^1$ is an hydrogen atom.

6. The nucleoside derivative or a salt thereof according to claim 1, wherein the atomic group having a sugar skeleton at a nucleoside residue or the atomic group having a sugar phosphate skeleton at a nucleotide residue is represented by the following chemical formula 2:

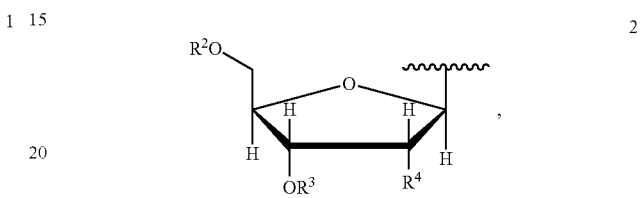

where in the chemical formula 2,
$R^2$ is a hydrogen atom, a protecting group, or a group represented by the following chemical formula 3,
$R^3$ is a hydrogen atom, a protecting group, or a phosphoramidite group,
$R^4$ is a hydrogen atom, a fluorine atom, a hydroxyl group, an amino group, or a mercapto group,

where in the chemical formula 3,
Y is an oxygen atom or a sulfur atom,
Z is a hydroxyl group or an imidazole group, and
m is an integer of 1 to 10.

7. The nucleoside derivative or a salt thereof according to claim 1, wherein the nucleoside derivative represented by the chemical formula 1 is a nucleoside derivative represented by the following chemical formula 4.

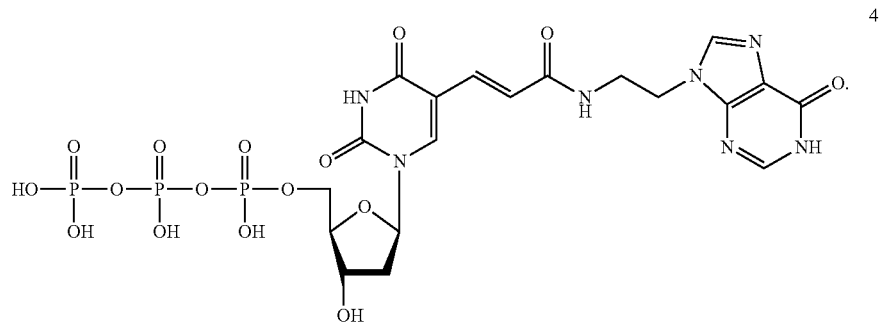 [SMILES: O=C(/C=C/c1cn([C@H]2C[C@@H](O)[C@@H](COP(=O)(O)OP(=O)(O)OP(=O)(O)O)O2)c(=O)[nH]c1=O)NCCn1cnc2c(=O)[nH]cnc21]

8. A polynucleotide synthesis reagent comprising a nucleotide derivative or a salt thereof that comprises the nucleoside derivative or a salt thereof, represented by the chemical formula 1 according to claim 1:

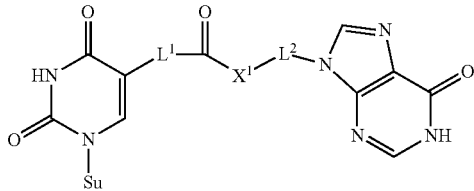

where in the chemical formula 1,
Su is an atomic group having a sugar skeleton at a nucleoside residue or an atomic group having a sugar phosphate skeleton at a nucleotide residue, and may or may not have a protecting group,
$L^1$ and $L^2$ are each independently a straight-chain or branched, saturated or unsaturated hydrocarbon group having 2 to 10 carbon atoms,
$X^1$ is an imino group (—$NR^1$—), an ether group (—O—), or a thioether group (—S—), and
$R^1$ is a hydrogen atom or a straight-chain or branched, saturated or unsaturated hydrocarbon group having 2 to 10 carbon atoms.

9. A method for producing a polynucleotide, comprising the step of synthesizing a polynucleotide using a nucleotide derivative or a salt thereof that comprises the nucleoside derivative or a salt thereof, represented by the chemical formula 1 according to claim 1:
where in the chemical formula 1,
Su is an atomic group having a sugar skeleton at a nucleoside residue or an atomic group having a sugar phosphate skeleton at a nucleotide residue, and may or may not have a protecting group,
$L^1$ and $L^2$ are each independently a straight-chain or branched, saturated or unsaturated hydrocarbon group having 2 to 10 carbon atoms,
$X^1$ is an imino group (—$NR^1$—), an ether group (—O—), or a thioether group (—S—), and
$R^1$ is a hydrogen atom or a straight-chain or branched, saturated or unsaturated hydrocarbon group having 2 to 10 carbon atoms.

10. A polynucleotide, comprising, as a building block, a nucleotide derivative or a salt thereof that comprises the nucleoside derivative or a salt thereof, represented by the chemical formula 1 according to claim 1:
where in the chemical formula 1,
Su is an atomic group having a sugar skeleton at a nucleoside residue or an atomic group having a sugar phosphate skeleton at a nucleotide residue, and may or may not have a protecting group,
$L^1$ and $L^2$ are each independently a straight-chain or branched, saturated or unsaturated hydrocarbon group having 2 to 10 carbon atoms,
$X^1$ is an imino group (—$NR^1$—), an ether group (—O—), or a thioether group (—S—), and
$R^1$ is a hydrogen atom or a straight-chain or branched, saturated or unsaturated hydrocarbon group having 2 to 10 carbon atoms.

11. The polynucleotide according to claim 10, wherein the polynucleotide is a binding nucleic acid molecule that binds to a target.

12. The polynucleotide according to claim 11, wherein the target is at least one of secretory immunoglobulin A or amylase.

13. A method for producing a binding nucleic acid molecule, comprising the steps of:
causing a candidate polynucleotide and a target to come into contact with each other; and
selecting a candidate polynucleotide bound to the target as a binding nucleic acid molecule that binds to the target, wherein
the candidate polynucleotide is the polynucleotide according to claim 10.

14. The method according to claim 13, wherein the target is at least one of secretory immunoglobulin A or amylase.

* * * * *